United States Patent
Agach et al.

(10) Patent No.: US 12,239,726 B2
(45) Date of Patent: *Mar. 4, 2025

(54) PROCESS FOR DYEING OR BLEACHING KERATIN FIBERS USING PARTICULAR AMINO ACIDS IN HIGH CONCENTRATION

(71) Applicant: L'Oreal, Paris (FR)

(72) Inventors: Mickaël Agach, Saint-Ouen (FR); Henri Samain, Chevilly Larue (FR); Simon Donck, Saint-Ouen (FR); Ambre Souvirou, Saint-Ouen (FR); Leila Hercouet, Saint-Ouen (FR)

(73) Assignee: L'OREAL, Paris (FR)

( * ) Notice: Subject to any disclaimer, the term of this patent is extended or adjusted under 35 U.S.C. 154(b) by 140 days.

This patent is subject to a terminal disclaimer.

(21) Appl. No.: 18/013,659

(22) PCT Filed: Jun. 30, 2021

(86) PCT No.: PCT/EP2021/068032
§ 371 (c)(1),
(2) Date: Dec. 29, 2022

(87) PCT Pub. No.: WO2022/003038
PCT Pub. Date: Jan. 6, 2022

(65) Prior Publication Data
US 2023/0172826 A1 Jun. 8, 2023

(30) Foreign Application Priority Data
Jun. 30, 2020 (FR) ..................................... 2006866
Dec. 11, 2020 (FR) ..................................... 2013092

(51) Int. Cl.
*A61Q 5/10* (2006.01)
*A61K 8/44* (2006.01)
*A61Q 5/08* (2006.01)
*A61Q 5/12* (2006.01)

(52) U.S. Cl.
CPC ............... *A61K 8/447* (2013.01); *A61Q 5/08* (2013.01); *A61Q 5/10* (2013.01); *A61Q 5/12* (2013.01); *A61K 2800/4324* (2013.01); *A61K 2800/87* (2013.01); *A61K 2800/884* (2013.01)

(58) Field of Classification Search
CPC ............ A61K 8/447; A61K 2800/4324; A61K 2800/87; A61K 2800/884; A61K 8/41; A61K 8/64; A61K 8/891; A61K 8/898; A61K 8/44; A61K 8/22; A61Q 5/08; A61Q 5/10; A61Q 5/12; A61Q 5/00
USPC .......................................................... 8/405
See application file for complete search history.

(56) References Cited

U.S. PATENT DOCUMENTS

| | | |
|---|---|---|
| 4,003,699 A | 1/1977 | Rose et al. |
| RE30,199 E | 1/1980 | Rose et al. |
| 5,046,516 A | 9/1991 | Barradas |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 5,957,140 A | 9/1999 | McGee |
| 6,099,592 A | 8/2000 | Vidal et al. |
| 6,284,003 B1 | 9/2001 | Rose et al. |
| 6,730,789 B1 | 5/2004 | Birault et al. |
| 8,257,447 B2 * | 9/2012 | Legrand ............... A61K 8/4946 8/606 |
| 8,343,237 B2 * | 1/2013 | Legrand ................. A61Q 5/065 8/405 |
| 11,389,387 B2 | 7/2022 | Haake et al. |
| 2005/0251928 A1 | 11/2005 | Kravtchenko et al. |
| 2009/0071494 A1 * | 3/2009 | Nguyen ................. A61K 8/736 132/202 |
| 2013/0156716 A1 * | 6/2013 | Yontz ....................... A61Q 5/10 8/405 |
| 2019/0184209 A1 | 6/2019 | Schroeder et al. |
| 2020/0163867 A1 * | 5/2020 | Viscogliosi ............. A61K 8/34 |

FOREIGN PATENT DOCUMENTS

| | | |
|---|---|---|
| DE | 2359399 A1 | 6/1975 |
| DE | 3843892 A1 | 6/1990 |
| DE | 4133957 A1 | 4/1993 |
| DE | 19543988 A1 | 5/1997 |
| DE | 102009027360 A1 | 1/2011 |
| DE | 102017223063 A1 | 6/2019 |
| EP | 0714954 A2 | 6/1996 |
| EP | 0770375 A1 | 5/1997 |
| FR | 2733749 A1 | 11/1996 |
| FR | 2801308 A1 | 5/2001 |
| FR | 2814948 A1 | 4/2002 |

(Continued)

OTHER PUBLICATIONS

International Search Report and Written Opinion for counterpart Application No. PCT/EP2021/068034, dated Aug. 27, 2021.
International Search Report and Written Opinion for counterpart Application No. PCT/EP2021/068032, dated Aug. 27, 2021.
Todd et al., "Volatile Silicone Fluids for Cosmetics," Cosmetics and Toiletries, vol. 91, Jan. 76, pp. 27-32.
Mintel: "Treatment," Kose Cosmeport Je L'Aime Amino Supreme Satin Sleek, Record No. 7462129, XP055784739, Mar. 1, 2020.
Mintel: "Conditioner," Kose Japan Stephen Knoll Premium Sleek Shine Repair Silky Smooth, Kose Japan, Record No. 3489415, XP055784742, Sep. 1, 2015.

(Continued)

*Primary Examiner* — Eisa B Elhilo
(74) *Attorney, Agent, or Firm* — THE MARBURY LAW GROUP, PLLC

(57) ABSTRACT

The present invention relates to a process for dyeing or bleaching keratin fibers, comprising the application to the keratin fibers of a composition comprising a high content of one or more particular amino acids followed by the application of a dyeing or bleaching composition.

20 Claims, No Drawings

(56) References Cited

FOREIGN PATENT DOCUMENTS

| FR | 2870119 A1 | 11/2005 | | |
|----|------------|---------|---|---|
| FR | 2886136 A1 | 12/2006 | | |
| FR | 2922444 A1 | 4/2009 | | |
| GB | 1026978 A | 4/1966 | | |
| GB | 1153196 A | 5/1969 | | |
| JP | 02-019576 A | 1/1990 | | |
| JP | 05-163124 A | 6/1993 | | |
| JP | 2009-107959 A | 5/2009 | | |
| WO | 94/08969 A1 | 4/1994 | | |
| WO | 94/08970 A1 | 4/1994 | | |
| WO | 95/01772 A1 | 1/1995 | | |
| WO | 95/15144 A1 | 6/1995 | | |
| WO | 96/15765 A1 | 5/1996 | | |
| WO | 2009/050295 A2 | 4/2009 | | |
| WO | WO 2017189574 A1 * | 11/2017 | ............... | A61Q 5/10 |
| WO | 2018/068947 A2 | 4/2018 | | |
| WO | 2019/012219 A1 | 1/2019 | | |
| WO | WO 2019234193 A1 * | 12/2019 | ............... | A61Q 5/10 |
| WO | 2022/003040 A1 | 1/2022 | | |

OTHER PUBLICATIONS

Mintel: "Infinite Strength Shampoo," Saint-Algue—SAF, Record No. 5012531, XP055784745, Aug. 1, 2017.

Mintel: "Treatment Mask," Kose Cosmeport Japan, Record ID 5412235, XP055784752, Jan. 1, 2018.

* cited by examiner

PROCESS FOR DYEING OR BLEACHING KERATIN FIBERS USING PARTICULAR AMINO ACIDS IN HIGH CONCENTRATION

CROSS REFERENCE TO RELATED APPLICATIONS

This is a National Stage Application of PCT/EP2021/068032, filed internationally on Jun. 30, 2021, which claims priority to French Application Nos. 2006866 and 2013092, filed on Jun. 30, 2020 and Dec. 11, 2020, respectively, the contents of all of which are incorporated by reference herein in their entireties.

FIELD OF THE INVENTION

The present invention relates to a process for dyeing or bleaching keratin fibers, comprising the application to the keratin fibers of a composition comprising a high content of one or more particular amino acids followed by the application of a dyeing or bleaching composition.

BACKGROUND OF THE INVENTION

It is known practice to perform hair dyeing or bleaching processes to modify the color of natural hair. These processes generally consist in applying to the keratin fibers hair compositions comprising chemical oxidizing agents and optionally direct dyes and/or oxidation dyes.

These dyeing or bleaching hair compositions do, admittedly, have dyeing or bleaching power, but they may occasionally be responsible for degradation of the quality of the fiber, the constituent proteins of the hair possibly being denatured, thus giving rise to labile proteins. The higher the content of labile proteins, the more the hair is damaged. This degradation of the fiber quality may result in substantial breakage during combing of the hair, notably when these compositions are applied to sensitized hair. Thus, it is common practice to resort to care compositions involving conditioning agents in order to limit the degradation or to improve the cosmetic properties of the hair. However, these care compositions may, in certain cases, impair the dyeing or bleaching of the keratin fibers thus treated.

There is thus a real need to develop a process for dyeing or bleaching keratin fibers, which makes it possible to conserve or even to improve the quality of the keratin fibers and notably to reduce the breakage thereof, while at the same time avoiding impairment of the dyeing or bleaching of the keratin fibers thus treated. Such a process must also involve compositions that are easy to use, notably easy to apply and stable and that make it possible to maintain or even to improve the cosmetic properties of the keratin fibers thus treated, for example as regards the sheen, the soft feel, the suppleness, the appearance or the disentangling. Furthermore, such a process will ideally need to be compatible with any type of dyeing or bleaching composition that is commercially available.

The Applicant has discovered, surprisingly, that all of these objectives can be achieved by means of the process according to the present invention.

SUMMARY OF THE INVENTION

According to a first aspect, a subject of the present invention is a process for dyeing or bleaching keratin fibers, comprising the following successive steps:

i) applying to the keratin fibers a composition (A) comprising one or more amino acids chosen from the compounds of formula ($I_1$), salts thereof and mixtures thereof:

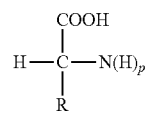

($I_1$)

in which formula ($I_1$):
p is an integer equal to 1 or 2;
when p=1, R forms with the nitrogen atom a saturated 5- to 8-membered, preferably 5-membered, heterocycle, this ring possibly being optionally substituted with at least one group chosen from hydroxyl or ($C_1$-$C_4$)alkyl;
when p=2, R represents:
a hydrogen atom; or
a ($C_1$-$C_{12}$)alkyl group, preferably a ($C_1$-$C_4$)alkyl group, interrupted with at least one heteroatom or group chosen from —S—, —NH— or —C(NH)— and/or substituted with at least one group chosen from hydroxyl, amino or —NH—C(NH)—$NH_2$;
the amino acid(s) being present in composition (A) in a total content of at least 5% by weight relative to the total weight of composition (A);
ii) applying to the keratin fibers a dyeing or bleaching composition.

According to a second aspect, a subject of the present invention is composition (A) as defined previously.

According to a third aspect, a subject of the present invention is the use of a composition (A) as defined previously, as a pretreatment composition of a dyeing or bleaching process.

According to a fourth aspect, a subject of the present invention is the use of a composition (A) as defined previously, for protecting keratin fibers, preferably for protecting them against breakage, during a dyeing or bleaching treatment.

According to a fifth aspect, a subject of the present invention is a multi-compartment device comprising:
a first compartment containing a composition (A) as defined previously; and
a second compartment containing a composition comprising at least one chemical oxidizing agent; and
optionally a third compartment containing a composition comprising at least one coloring agent chosen from oxidation dyes, direct dyes and mixtures thereof.

DETAILED DESCRIPTION OF THE INVENTION

For the purposes of the present invention and unless otherwise indicated: the term "keratin fibers" means fibers of human or animal origin, such as head hair, bodily hair, the eyelashes, the eyebrows, wool, angora, cashmere or fur. According to the present invention, the keratin fibers are preferably human keratin fibers, more preferentially the hair.
the term "successive steps" means steps performed in the indicated order.
the term "dye composition" means a composition comprising at least one coloring agent.

the term "bleaching composition" means a composition comprising at least one chemical oxidizing agent.

the term "alkyl group" means a linear or branched, saturated hydrocarbon-based radical.

the term "$(C_x-C_y)$alkyl group" means an alkyl group comprising from x to y carbon atoms.

the term "coloring agent" means an oxidation dye, a direct dye or a pigment.

the term "oxidation dye" means an oxidation dye precursor chosen from oxidation bases and couplers. Oxidation bases and couplers are colorless or sparingly colored compounds, which, via a condensation reaction in the presence of an oxidizing agent, give a colored species.

the term "direct dye" means a natural and/or synthetic dye, including in the form of an extract or extracts, other than oxidation dyes. These are colored compounds that will spread superficially on the fiber. They may be ionic or nonionic, i.e. anionic, cationic, neutral or nonionic.

the term "reducing agent" means an agent that is capable of reducing the disulfide bonds of the hair, such as compounds chosen from thiols, alkaline sulfites, hydrides and phosphines.

the term "chemical oxidizing agent" means an oxidizing agent other than atmospheric oxygen.

Unless otherwise indicated, when compounds are mentioned in the present patent application, this also includes the optical isomers thereof, the geometrical isomers thereof, the tautomers thereof, the salts thereof or the solvates thereof, alone or as a mixture.

The expressions "at least one" and "one or more" are synonymous and may be used interchangeably.

Process for Dyeing or Bleaching Keratin Fibers

According to a first aspect, a subject of the present invention is a process for dyeing or bleaching keratin fibers as defined previously.

The Applicant has found, surprisingly, that the process according to the invention makes it possible to conserve or even to improve the quality of the keratin fibers and to reduce the breakage thereof, while at the same time avoiding impairment of the dyeing or bleaching. Furthermore, the process according to the invention involves a pretreatment step with a composition which is different from the dyeing or bleaching composition and is thus compatible with any type of dyeing or bleaching composition available on the market.

In the process according to the present invention, it is essential for steps i) and ii) to be successive, i.e. for step ii) to be performed after step i).

The process may comprise one or more additional steps between steps i) and ii), but, even in such an embodiment, step ii) is always performed after step i).

Composition (A)

Amino Acids

Composition (A) applied to the keratin fibers during step i) of the process comprises one or more amino acids chosen from the compounds of formula $(I_1)$ as defined previously, salts thereof and mixtures thereof, preferably chosen from the compounds of formula $(I_1)$.

The salts of compounds of formula $(I_1)$ comprise the salts with organic or mineral bases, for example the salts of alkali metals, for instance the lithium, sodium or potassium salts; the salts of alkaline-earth metals, for instance the magnesium or calcium salts, and the zinc salts.

The compounds of formula $(I_1)$ may be in the form of an optical isomer of L, D or DL configuration, preferably of L configuration.

As examples according to the present invention of compounds of formula $(I_1)$ in the form of an optical isomer of L configuration, mention may be made of L-proline, L-methionine, L-serine, L-arginine and L-lysine.

Preferably, the amino acid(s) included in composition (A) are chosen from glycine, proline, methionine, serine, arginine, lysine, salts thereof and mixtures thereof.

More preferentially, the amino acid(s) included in composition (A) are chosen from glycine, proline, methionine, serine, salts thereof and mixtures thereof.

Even more preferentially, the amino acid included in composition (A) is chosen from glycine, salts thereof and mixtures thereof.

As examples of glycine salts that may be used in the present invention mention may be made of sodium glycinate, zinc glycinate, calcium glycinate, magnesium glycinate, manganese glycinate and potassium glycinate, preferably sodium glycinate or potassium glycinate.

Particularly preferably, the amino acid included in composition (A) is glycine.

The amino acid(s) chosen from the compounds of formula $(I_1)$, salts thereof and mixtures thereof are present in composition (A) in a total content of at least 5% by weight, preferably of at least 8% by weight, relative to the total weight of composition (A).

The amino acid(s) chosen from the compounds of formula $(I_1)$, salts thereof and mixtures thereof may be present in composition (A) in a total content ranging from 5% to 20% by weight, preferably ranging from 5% to 15% by weight, more preferentially ranging from 8% to 12% by weight, relative to the total weight of composition (A).

Composition (A) may preferably comprise at least 5% by weight, more preferentially at least 8% by weight, of glycine, salts thereof and mixtures thereof relative to the total weight of composition (A).

Preferably, composition (A) comprises from 5% to 20% by weight, preferably from 5% to 15% by weight and more preferentially from 8% to 12% by weight of glycine, salts thereof and mixtures thereof relative to the total weight of composition (A).

According to a preferred embodiment, composition (A) applied to the keratin fibers during step i) of the process comprises one or more amino acids chosen from the compounds of formula $(I_1)$ as defined previously.

According to this preferred embodiment, the amino acid(s) included in composition (A) are preferably chosen from glycine, proline, methionine, serine, arginine, lysine and mixtures thereof, more preferentially from glycine, proline, methionine, serine and mixtures thereof, and, even more preferentially, the amino acid included in composition (A) is glycine.

According to this preferred embodiment, the amino acid(s) chosen from the compounds of formula $(I_1)$ are present in composition (A) in a total content of at least 5% by weight, preferably of at least 8% by weight, relative to the total weight of composition (A).

According to this preferred embodiment, the amino acid(s) chosen from the compounds of formula $(I_1)$ are present in composition (A) in a total content preferably ranging from 5% to 20% by weight, more preferentially ranging from 5% to 15% by weight, even more preferentially ranging from 8% to 12% by weight, relative to the total weight of composition (A).

According to this preferred embodiment, composition (A) may preferably comprise at least 5% by weight, more preferentially at least 8% by weight, of glycine relative to the total weight of composition (A).

According to this preferred embodiment, composition (A) preferably comprises from 5% to 20% by weight, more preferentially from 5% to 15% by weight and even more preferentially from 8% to 12% by weight of glycine relative to the total weight of composition (A).

pH

Composition (A) may have a pH ranging from 2 to 11. Preferably, the pH of composition (A) ranges from 4 to 10. More preferentially, the pH of composition (A) ranges from 8 to 10. By way of example, the pH of composition (A) may be equal to 9.

The pH of composition (A) may be adjusted with at least one organic or mineral acid, or with at least one alkaline agent chosen from mineral or organic or hybrid alkaline agents and mixtures thereof.

The term "organic acid" means an acid, i.e. a compound that is capable of releasing a cation or proton $H^+$ or $H_3O^+$, in aqueous medium, which includes at least one optionally unsaturated, linear or branched $C_1$-$C_{20}$ hydrocarbon-based chain, a (hetero)cycloalkyl or (hetero)aryl group and at least one acidic chemical function chosen in particular from carboxyl C(O)OH, sulfonic $SO_3H$, sulfinic $SO_2H$, phosphonic $POSH$ and phosphinic $PO_2H_2$.

More particularly, the organic or mineral acid used is chosen from hydrochloric acid HCl, hydrobromic acid HBr, sulfuric acid $H_2SO_4$, alkylsulfonic acids: $(C_1$-$C_6)$Alk-$S(O)_2OH$ such as methylsulfonic acid and ethylsulfonic acid; arylsulfonic acids: Ar—$S(O)_2OH$ such as benzenesulfonic acid and toluenesulfonic acid; $(C_1$-$C_6)$alkoxysulfinic acids: Alk-O—$S(O)OH$ such as methoxysulfinic acid and ethoxysulfinic acid; aryloxysulfinic acids such as tolueneoxysulfinic acid and phenoxysulfinic acid; phosphoric acid $H_3PO_4$; triflic acid $CF_3SO_3H$ and tetrafluoroboric acid $HBF_4$, and carboxylic acid(s) of formula (II) below and the salts thereof:

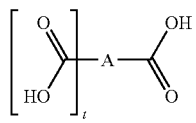

(II)

in which formula (II):

A represents a saturated or unsaturated, cyclic or noncyclic, aromatic or nonaromatic hydrocarbon-based group, which is monovalent when t is 0 or polyvalent when t is greater than or equal to 1, comprising from 1 to 50 carbon atoms, which is optionally interrupted with one or more heteroatoms and/or optionally substituted, notably with one or more hydroxyl groups; preferably, A represents a monovalent $(C_1$-$C_6)$alkyl group or a polyvalent $(C_1$-$C_6)$alkylene group optionally substituted with one or more hydroxyl groups.

In particular, the acid used is chosen from the carboxylic acids of formula (II) as defined previously. Preferably, the acid used is an α-hydroxy acid such as lactic acid, glycolic acid, tartaric acid or citric acid.

The mineral alkaline agents are preferably chosen from aqueous ammonia, alkaline carbonates or bicarbonates such as sodium or potassium carbonates and sodium or potassium bicarbonates, sodium hydroxide or potassium hydroxide, and mixtures thereof.

The organic alkaline agents are preferably chosen from organic amines, i.e. they contain at least one substituted or unsubstituted amino group.

The organic alkaline agents are more preferentially chosen from organic amines with a $pK_b$ at 25° C. of less than 12, preferably of less than 10 and even more advantageously of less than 6. It should be noted that it is the $pK_b$ corresponding to the function which has the highest basicity.

The organic alkaline agents are chosen, for example, from alkanolamines, oxyethylenated and/or oxypropylenated ethylenediamines and the compounds of formula (III) below:

(III)

in which formula (III):

W is a divalent $C_1$-$C_6$ alkylene group optionally substituted with a hydroxyl group or a $(C_1$-$C_6)$alkyl group, and/or optionally interrupted with one or more heteroatoms such as oxygen or $NR^u$;

$R^x$, $R^y$, $R^z$ $R^t$ and $R^u$, which may be identical or different, represent a hydrogen atom or a group chosen from $(C_1$-$C_6)$alkyl, $C_1$-$C_6$ hydroxyalkyl or $C_1$-$C_6$ aminoalkyl.

Preferably, the alkanolamine is ethanolamine (or monoethanolamine).

In one variant of the invention, composition (A) comprises, as alkaline agent, one or more alkanolamines (preferably ethanolamine) and aqueous ammonia. In this variant, the alkanolamine(s) are present in a predominant amount relative to the aqueous ammonia.

Hybrid alkaline agents that may be mentioned include the salts of the amines mentioned previously with acids such as carbonic acid or hydrochloric acid.

Cationic Polymers

Composition (A) may comprise one or more cationic polymers.

The term "cationic polymer" means any polymer comprising cationic groups and/or groups that can be ionized into cationic groups and not comprising any anionic groups and/or groups that can be ionized into anionic groups. Preferably, the cationic polymer is hydrophilic or amphiphilic.

The preferred cationic polymers are chosen from those that contain units including primary, secondary, tertiary and/or quaternary amine groups that may either form part of the main polymer chain or may be borne by a side substituent directly connected thereto. The cationic polymers that may be used preferably have a weight-average molar mass (Mw) ranging from 500 to $5 \times 10^6$ g/mol and preferably ranging from $10^3$ to $3 \times 10^6$ g/mol. Preferably, composition (A) comprises one or more cationic polymers chosen from homopolymers or copolymers including in their structure one or more units corresponding to formula (I) or (II):

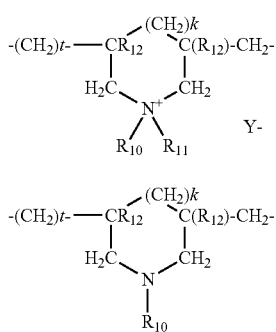

(I)

(II)

in which:
k and t are equal to 0 or 1, the sum k+t being equal to 1;
$R_{12}$ denotes a hydrogen atom or a methyl group;
$R_{10}$ and $R_{11}$, independently of each other, denote a $(C_1-C_6)$alkyl group, a $C_1-C_5$ hydroxyalkyl group, a $C_1-C_4$ amidoalkyl group; or alternatively $R_{10}$ and $R_{11}$ denote, together with the nitrogen atom to which they are attached, a heterocyclic group such as piperidyl or morpholinyl; preferably, $R_{10}$ and $R_{11}$, independently of each other, denote a $(C_1-C_4)$alkyl group;
$Y^-$ is an anion preferably chosen from bromide, chloride, acetate, borate, citrate, tartrate, bisulfate, bisulfite, sulfate and phosphate.

More preferentially, composition (A) comprises one or more cationic polymers chosen from homopolymers or copolymers including in their structure one or more units corresponding to formula (I) as defined previously.

Even more preferentially, composition (A) comprises one or more cationic polymers chosen from homopolymers of diallyldimethylammonium salts and copolymers of diallyldimethylammonium salts and of acrylamide.

Particularly preferably, composition (A) comprises one or more cationic polymers chosen from copolymers of diallyldimethylammonium salts and of acrylamide.

Mention may be made more particularly of the homopolymer of dimethyldiallylammonium salts (for example chloride) for example sold under the name Merquat 100 by the company Nalco and the copolymers of diallyldimethylammonium salts (for example chloride) and of acrylamide, notably sold under the name Merquat 550 or Merquat 7SPR.

The cationic polymer(s) may be present composition (A) in a total content ranging from 0.00001% to 5% by weight, preferably ranging from 0.00005% to 1% by weight and more preferentially ranging from 0.00007% to 0.5% by weight, relative to the total weight of composition (A).

Amino Silicones.

Composition (A) may comprise one or more silicones, preferably chosen from amino silicones.

The term "amino silicone" means any silicone including at least one primary, secondary or tertiary amine function.

The weight-average molecular masses of these amino silicones may be measured by gel permeation chromatography (GPC) at room temperature (25° C.), as polystyrene equivalent. The columns used are μ styragel columns. The eluent is THF and the flow rate is 1 ml/min. 200 μl of a 0.5% by weight solution of silicone in THF are injected. Detection is performed by refractometry and UV-metry.

Preferably, the amino silicones are chosen from the amino silicones of formula (B) below:

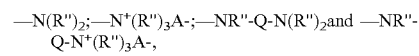

(B)

in which:
G, which may be identical or different, denotes a hydrogen atom or a group from among phenyl, OH, $C_1-C_8$ alkyl, for example methyl, or $C_1-C_8$ alkoxy, for example methoxy;
a, which may be identical or different, denotes 0 or an integer from 1 to 3, in particular 0;
b denotes 0 or 1, in particular 1;
m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;
R', which may be identical or different, denotes a monovalent radical of formula
CqH2qL in which q is a number ranging from 2 to 8 and L is an optionally quaternized amine group chosen from the following groups:

—N(R")$_2$;—N$^+$(R")$_3$A-;—NR"-Q-N(R")$_2$ and —NR"-Q-N$^+$(R")$_3$A-, in which R", which may be identical or different, denotes hydrogen, phenyl, benzyl, or a saturated monovalent hydrocarbon-based radical, for example a $C_1-C_{20}$ alkyl radical; Q denotes a linear or branched group of formula $C_rH_{2r}$, r being an integer ranging from 2 to 6, preferably from 2 to 4; and A$^-$ represents a cosmetically acceptable anion, notably a halide such as fluoride, chloride, bromide or iodide.

More preferentially, the amino silicones are chosen from the amino silicones of formula (F) below:

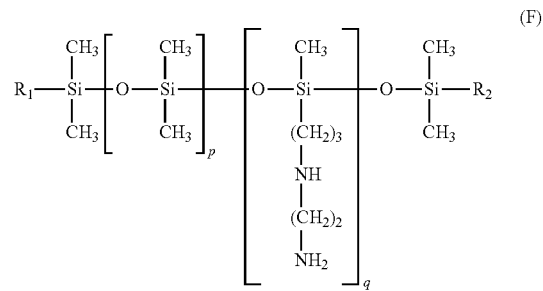

(F)

in which:
p and q are numbers such that the sum (p+q) ranges from 1 to 1000, in particular from 50 to 350 and more particularly from 150 to 250; p possibly denoting a number from 0 to 999, notably from 49 to 349 and more particularly from 159 to 239, and q possibly denoting a number from 1 to 1000, notably from 1 to 10 and more particularly from 1 to 5;
$R_1$ and $R_2$, which are different, represent a hydroxyl or $C_1-C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular mass (Mw) of the silicone preferably ranges from 2000 to 200 000, even more particularly from 5000 to 100 000 and more particularly from 10 000 to 50 000.

The commercial products comprising silicones of structure (F) may include in their composition one or more other amino silicones whose structure is different from that of formula (F).

A product containing amino silicones of structure (F) is sold by Wacker under the name Fluid WR 1300®.

Among the amino silicones of formula (F), mention may also be made of the product Belsil ADM Log 1 from Wacker.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometers.

The silicone(s) may be present in composition (A) in a total content ranging from 0.001% to 10% by weight, preferably ranging from 0.01% to 5% by weight, more preferentially ranging from 0.02% to 1% by weight, even more preferentially ranging from 0.05% to 0.5% by weight relative to the total weight of composition (A).

The amino silicone(s) may be present composition (A) in a total content ranging from 0.001% to 10% by weight, preferably ranging from 0.01% to 5% by weight, more preferentially from 0.02% to 1% by weight and even more preferentially ranging from 0.05% to 0.5% by weight, relative to the total weight of composition (A).

Composition (A) preferably comprises a total content of coloring agents and/or reducing agents of less than 0.1% by weight, more preferentially less than 0.01% by weight, even more preferentially less than 0.001% by weight, relative to the total weight of composition (A).

According to a particularly preferred embodiment, composition (A) is free of coloring agents and/or reducing agents.

Composition (A) preferably comprises a total content of chemical oxidizing agents of less than 0.1% by weight, more preferentially less than 0.01% by weight, even more preferentially less than 0.001% by weight, relative to the total weight of composition (A).

Surfactants

Composition (A) preferably comprises less than 5% by weight, more preferentially less than 2% by weight and even more preferentially less than 1% by weight of surfactants relative to the total weight of composition (A).

In particular, composition (A) may comprise a total content of anionic surfactants of less than 0.1% by weight, preferably less than 0.01% by weight, more preferentially less than 0.001% by weight, relative to the total weight of composition (A).

According to a particularly preferred embodiment, composition (A) is free of anionic surfactants.

Composition (A) may comprise a total content of nonionic surfactants of less than 0.5% by weight relative to the total weight of composition (A).

Water

Composition (A) may comprise a total content of water ranging from 1% to 95% by weight, preferably ranging from 20% to 95%, more preferentially ranging from 40% to 90% by weight and even more preferentially ranging from 60% to 85% by weight, relative to the total weight of composition (A).

Organic Solvents

Composition (A) may comprise at least one organic solvent, preferably chosen from monoalcohols, polyols, polyol ethers and mixtures thereof.

Composition (A) may comprise at least 5% by weight and preferably at least 8% by weight, relative to the total weight of composition (A), of one or more monoalcohols. The monoalcohols may be linear or branched.

The monoalcohols are preferably chosen from $C_2$ to $C_6$ monoalcohols, more preferentially from $C_2$ to $C_4$ monoalcohols, even more preferentially from ethanol, isopropanol, tert-butanol, n-butanol and mixtures thereof.

According to a particularly preferred embodiment, the monoalcohol is ethanol.

The monoalcohol(s) may be present in composition (A) in a total content ranging from 5% to 20% by weight, preferably ranging from 5% to 15% by weight, more preferentially ranging from 8% to 12% by weight, relative to the total weight of composition (A).

The polyols are preferably chosen from propylene glycol, dipropylene glycol, glycerol and mixtures thereof.

The polyol ethers are preferably chosen from propylene glycol monomethyl ether, diethylene glycol monomethyl ether and monoethyl ether and mixtures thereof.

Composition (A) may comprise a total content of organic solvents ranging from 1% to 40% by weight, preferably ranging from 5% to 30% by weight, more preferentially ranging from 8% to 15% by weight, relative to the total weight of the composition.

Dyeing or Bleaching Composition

Chemical Oxidizing Agent

The dyeing or bleaching composition applied to the keratin fibers during step ii) of the process may comprise at least one chemical oxidizing agent.

Preferably, the chemical oxidizing agent is chosen from hydrogen peroxide, urea peroxide, alkali metal bromates, peroxygenated salts, peracids and precursors thereof, and mixtures thereof.

Most preferentially, the chemical oxidizing agent is chosen from hydrogen peroxide, peroxygenated salts, and mixtures thereof.

Even more preferentially, the chemical oxidizing agent is chosen from hydrogen peroxide, persulfates, perborates or percarbonates of alkali metals or alkaline-earth metals or of ammonium, and mixtures thereof.

Most preferentially, the chemical oxidizing agent is hydrogen peroxide.

Examples of peroxygenated salts that may be mentioned include sodium, potassium or ammonium persulfates and mixtures thereof.

When the composition is a bleaching composition, it may preferably comprise hydrogen peroxide and a peroxygenated salt.

The dyeing or bleaching composition may comprise a total content of chemical oxidizing agents ranging from 0.5% to 60% by weight, preferably ranging from 0.5% to 40% by weight, more preferentially ranging from 1% to 30% by weight, relative to the total weight of the dyeing or bleaching composition.

Liquid Fatty Substances

The dyeing or bleaching composition may also comprise one or more fatty substances that are liquid at room temperature (25° C.) and at atmospheric pressure ($1.013 \times 10^5$ Pa), other than salified fatty acids.

The term "fatty substance" means an organic compound that is insoluble in water at room temperature (25° C.) and at atmospheric pressure ($1.013 \times 10^5$ Pa) (solubility of less than 5% by weight, preferably less than 1% by weight and even more preferentially less than 0.1% by weight). They bear in their structure at least one hydrocarbon-based chain including at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The term "oil" means a "fatty substance" that is liquid at room temperature (25° C.) and at atmospheric pressure ($1.013 \times 10^5$ Pa).

The term "nonsilicone fatty substance" refers to a fatty substance not containing any Si—O bonds and the term "silicone fatty substance" refers to a fatty substance containing at least one Si—O bond.

The liquid fatty substances that may be used in the dyeing or bleaching composition are different from salified fatty acids, i.e. they can be present in the composition in the form of free fatty acids. In other words, these fatty substances do not contain any salified carboxylic acid groups (—C(O)O—). In particular, these fatty substances are neither polyoxyethylenated nor polyglycerolated.

Preferably, the fatty substances are different from nonsalified fatty acids.

More particularly, the liquid fatty substances according to the invention are chosen from $C_6$ to $C_{16}$ liquid hydrocarbons, liquid hydrocarbons comprising more than 16 carbon atoms, nonsilicone oils of animal origin, oils of triglyceride type of plant or synthetic origin, fluoro oils, liquid fatty alcohols, liquid fatty acid and/or fatty alcohol esters other than triglycerides, and silicone oils, and mixtures thereof.

It is recalled that the fatty alcohols and esters more particularly contain at least one saturated or unsaturated, linear or branched hydrocarbon-based group, comprising 6 to 30 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the $C_6$ to $C_{16}$ liquid hydrocarbons, they are linear, branched or optionally cyclic, and are preferably alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly, polydecenes, hydrogenated polyisobutene such as Parleam®, and mixtures thereof.

A hydrocarbon-based oil of animal origin that may be mentioned is perhydrosqualene. The triglyceride oils of plant or synthetic origin are preferably chosen from liquid fatty acid triglycerides including from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stéarinerie Dubois or those sold under the names Miglyol® 810, 812 and 818 by the company Dynamit Nobel, jojoba oil and shea butter oil, and mixtures thereof.

As regards the fluoro oils, they may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylperfluoromorpholine sold under the name PF 5052® by the company 3M. The liquid fatty alcohols may more particularly be chosen from linear or branched, saturated or unsaturated alcohols, preferably unsaturated or branched alcohols, including from 6 to 30 carbon atoms and preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or fatty alcohols other than the triglycerides mentioned above, mention may be made notably of esters of saturated or unsaturated, linear $C_1$ to $C_{26}$ or branched $C_3$ to $C_{26}$ aliphatic monoacids or polyacids and of saturated or unsaturated, linear $C_1$ to $C_{26}$ or branched $C_3$ to $C_{26}$ aliphatic monoalcohols or polyalcohols, the total carbon number of the esters being greater than or equal to 6 and more advantageously greater than or equal to 10.

Preferably, for the esters of monoalcohols, at least one from among the alcohol and the acid from which the esters of the invention are derived is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononanoate; octyldodecyl erucate; oleyl erucate; ethyl palmitate, isopropyl palmitate, 2-ethylhexyl palmitate, 2-octyldecyl palmitate, alkyl myristates such as isopropyl 2-octyldodecyl myristate, isobutyl stearate; 2-hexyldecyl laurate, and mixtures thereof.

Preferably, among the monoesters of monoacids and of monoalcohols, use will be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Still within the context of this variant, use may also be made of esters of $C_4$ to $C_{22}$ dicarboxylic or tricarboxylic acids and of $C_1$ to $C_{22}$ alcohols and esters of mono-, di- or tricarboxylic acids and of $C_2$ to $C_{26}$ di-, tri-, tetra- or pentahydroxy alcohols.

Mention may notably be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The dyeing or bleaching composition may also comprise, as fatty ester, sugar esters and diesters of $C_6$ to $C_{30}$ and preferably $C_{12}$ to $C_{22}$ fatty acids. It is recalled that the term "sugar" refers to oxygen-bearing hydrocarbon-based compounds bearing several alcohol functions, with or without aldehyde or ketone functions, and which include at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, notably alkyl derivatives, such as methyl derivatives, for instance methylglucose.

The sugar esters of fatty acids may be chosen notably from the group comprising the esters or mixtures of esters of sugars described previously and of linear or branched, saturated or unsaturated $C_6$ to $C_{30}$ and preferably $C_{12}$ to $C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof notably such as the mixed oleo-palmitate, oleo-stearate and palmito-stearate esters More particularly, use is made of monoesters and diesters notably of sucrose, glucose or methylglucose mono- or di-oleates, stearates, behenates, oleopalmitates, linoleates, linolenates and oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

The silicone oils that may be used in the dyeing or bleaching composition may be volatile or nonvolatile, cyclic, linear or branched silicone oils, which are unmodified or modified with organic groups, and preferably have a viscosity from $5 \times 10^{-6}$ to 2.5 $m^2/s$ at 25° C., and preferably $1 \times 10^{-5}$ to 1 $m^2/s$.

Preferably, the silicone oils are chosen from polydialkylsiloxanes, notably polydimethylsiloxanes (PDMS), and liquid polyorganosiloxanes including at least one aryl group.

These silicone oils may also be organomodified. The organomodified silicone oil(s) that may be used in the dyeing or bleaching composition are preferably liquid silicones as defined previously and including in their structure one or more organofunctional groups attached via a hydrocarbon-based group, chosen, for example, from amine groups and alkoxy groups.

Organopolysiloxanes are defined in greater detail in Walter Noll's *Chemistry and Technology of Silicones* (1968), Academic Press. They may be volatile or nonvolatile.

When they are volatile, the silicone oils are more particularly chosen from those with a boiling point of between 60° C. and 260° C., and even more particularly from:

(i) cyclic polydialkylsiloxanes including from 3 to 7 and preferably from 4 to 5 silicon atoms. These are, for example, octamethylcyclotetrasiloxane notably sold under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide.

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ $m^2/s$ at 25° C. An example is decamethyltetrasiloxane notably sold under the name SH 200 by the company Toray Silicone. Silicones falling within this category are also described in the article published in Cosmetics and Toiletries, Vol. 91, Jan. 76, pages 27-32—Todd & Byers *Volatile Silicone Fluids for Cosmetics*.

Nonvolatile polydialkylsiloxanes are preferably used.

These silicone oils are more particularly chosen from polydialkylsiloxanes, among which mention may be made mainly of polydimethylsiloxanes bearing trimethylsilyl end groups.

The viscosity of the silicones is measured at 25° C. according to ASTM standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 $mm^2/s$;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

The organomodified silicones that may be used in the dyeing or bleaching composition are silicones as defined previously and including in their structure one or more organofunctional groups attached via a hydrocarbon-based group.

As regards the liquid polyorganosiloxanes including at least one aryl group, they may notably be polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ $m^2/s$ at 25° C.

Among these polyalkylarylsiloxanes, examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000:

certain oils of the SF series from General Electric, such as SF 1023, SF 1154, SF 1250 and SF 1265.

Among the organomodified silicones, mention may be made of polyorganosiloxanes including:

substituted or unsubstituted amine groups, such as the products sold under the names GP 4 Silicone Fluid and GP 7100 by the company Genesee or the products sold under the names Q2 8220 and Dow Corning 929 or 939 by the company Dow Corning. The substituted amine groups are, in particular, $C_1$ to $C_4$ aminoalkyl groups; alkoxy groups; hydroxyl groups.

The liquid fatty substance(s) are preferentially chosen from liquid hydrocarbons containing more than 16 carbon atoms, plant oils, liquid fatty alcohols and liquid fatty esters, silicone oils and mixtures thereof.

Preferentially, the liquid fatty substance(s) are chosen from liquid hydrocarbons comprising more than 16 carbon atoms, in particular liquid petroleum jelly.

In a particular embodiment, the total content of liquid fatty substance(s) included in the dyeing or bleaching composition is greater than or equal to 20% by weight, preferably greater than or equal to 30% by weight, more preferentially greater than or equal to 35% by weight, relative to the total weight of the dyeing or bleaching composition.

More preferentially, the total content of liquid fatty substance(s) included in the dyeing or bleaching composition ranges from 20% to 80% by weight, and preferably from 30% to 70% by weight, relative to the total weight of the dyeing or bleaching composition.

Alkaline Agents

The dyeing or bleaching composition may optionally also comprise one or more alkaline agents.

Preferably, the dyeing or bleaching composition comprises one or more organic or mineral alkaline agents.

The mineral alkaline agent(s) are preferably chosen from aqueous ammonia, alkali metal carbonates or bicarbonates such as sodium or potassium carbonates and sodium or potassium bicarbonates, sodium or potassium hydroxide, alkali metal silicates or metasilicates such as sodium or potassium silicates or metasilicates, or mixtures thereof.

The organic alkaline agent(s) are preferably chosen from organic amines with a $pK_b$ at 25° C. of less than 12, preferably less than 10 and even more advantageously less than 6. It should be noted that it is the $pK_b$ corresponding to the function which has the highest basicity. In addition, the organic amines do not comprise any alkyl or alkenyl fatty chains comprising more than ten carbon atoms.

The organic alkaline agent(s) are chosen, for example, from alkanolamines, oxyethylenated and/or oxypropylenated ethylenediamines, amino acids and the compounds of formula (III) below:

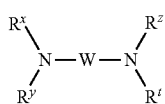
(III)

in which formula (III):

W is a divalent $C_1$-$C_6$ alkylene group optionally substituted with a hydroxyl group or a ($C_1$-$C_6$)alkyl group, and/or optionally interrupted with one or more heteroatoms such as oxygen or NR";

$R^x$, $R^y$, $R^z$ $R^t$ and $R^u$, which may be identical or different, represent a hydrogen atom or a group chosen from ($C_1$-$C_6$)alkyl, $C_1$-$C_6$ hydroxyalkyl or $C_1$-$C_6$ aminoalkyl.

Examples of amines of formula (III) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and include at least one acid function chosen more particularly from carboxylic acid, sulfonic acid, phosphonic acid and phosphoric acid functions. The amino acids may be in neutral or ionic form.

As amino acids that may be used in the dyeing or bleaching composition, mention may notably be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (IV) below, and also salts thereof:

R—$CH_2$—CH($NH_2$)—C(O)—OH     (IV)

in which R represents a group chosen from imidazolyl, preferably imidazolyl-4-yl; aminopropyl; aminoethyl; —($CH_2$)$_2$N(H)—C(O)—$NH_2$; and —($CH_2$)$_2$—N(H)—C(NH)—$NH_2$.

The compounds corresponding to formula (IV) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may notably be made of carnosine, anserine and balenine.

The organic amine may also be chosen from compounds including a guanidine function. As amines of this type that may be used in the present invention, besides arginine, which has already been mentioned as an amino acid, mention may be made notably of creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino(imino) methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular. Preferably, the alkaline agent(s) present in the dyeing or bleaching composition are chosen from aqueous ammonia, alkanolamines, alkali metal silicates, alkali metal metasilicates and mixtures thereof.

More preferentially, the alkaline agent present in the dyeing composition is monoethanolamine.

More preferentially, the alkaline agent present in the bleaching composition is chosen from sodium silicate, sodium metasilicate and mixtures thereof.

The total content of alkaline agents included in the dyeing or bleaching composition may range from 0.01% to 30% by weight, and preferably from 0.1% to 20% by weight, relative to the total weight of the dyeing or bleaching composition.

Solvents

The dyeing or bleaching composition may optionally also comprise one or more organic solvents.

Examples of organic solvents that may be mentioned include linear or branched $C_2$ to $C_4$ alkanols, such as ethanol and isopropanol; glycerol; polyols and polyol ethers, for instance 2-butoxyethanol, propylene glycol, hexylene glycol, dipropylene glycol, propylene glycol monomethyl ether, diethylene glycol monomethyl ether and monoethyl ether, and also aromatic alcohols or ethers, such as benzyl alcohol or phenoxyethanol, and mixtures thereof.

The organic solvent(s) may be present in the dyeing or bleaching composition in a content ranging from 0.01% to 30% by weight, preferably ranging from 2% to 25% by weight, relative to the total weight of the dyeing or bleaching composition.

Dye Composition

According to a particular embodiment of the invention, the composition applied to the keratin fibers during step ii) of the process is a dye composition.

The dye composition may comprise at least one coloring agent chosen from oxidation dyes, direct dyes, and mixtures thereof, preferably from oxidation dyes.

Oxidation Dyes

The oxidation dyes are generally chosen from one or more oxidation bases optionally combined with one or more coupling agents (also known as couplers).

Oxidation Bases

The dye composition may optionally comprise one or more oxidation bases advantageously chosen from those conventionally used in the dyeing of keratin fibers.

By way of example, the oxidation bases are chosen from para-phenylenediamines, bis(phenyl)alkylenediamines, para-aminophenols ortho-aminophenols and heterocyclic bases, and the corresponding addition salts.

Among the para-phenylenediamines that may be mentioned are, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(p-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N-ethyl-N—(β-hydroxyethyl)-para-phenylenediamine, N—(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N—(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the corresponding addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the corresponding addition salts with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the corresponding addition salts.

Among the para-aminophenols that are mentioned are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(p-hydroxyethylaminomethyl)phenol and 4-amino-2-fluorophenol, and the corresponding addition salts with an acid.

Among the ortho-aminophenols that may be mentioned, for example, are 2-aminophenol, 2-amino-5-methylphenol, 2-amino-6-methylphenol and 5-acetamido-2-aminophenol, and the corresponding addition salts.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-p-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1, 5-a]pyridines and are preferably substituted on carbon atom 2 with:
a) a (di)($C_1$-$C_6$)(alkyl)amino group, said alkyl group possibly being substituted with at least one hydroxyl, amino or imidazolium group;
b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or
c) a ($C_1$-$C_6$)alkoxy group optionally substituted with one or more hydroxyl groups, such as a β-hydroxyalkoxy group, and the corresponding addition salts.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the corresponding addition salts. Use may also be made of 4,5-diamino-1-(p-methoxyethyl)pyrazole.

A 4,5-diaminopyrazole will preferably be used and even more preferentially 4,5-diamino-1-(β-hydroxyethyl)pyrazole and/or a corresponding salt.

The pyrazole derivatives that may also be mentioned comprise diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt.

Heterocyclic bases that will preferably be used are 4,5-diamino-1-(R-hydroxyethyl)pyrazole and/or 2,3-diamino-6,7-dihydro-1H,5H-pyrazolo[1,2-a]pyrazol-1-one and/or a corresponding salt.

Coupling Agents

The dye composition may optionally comprise one or more coupling agents advantageously chosen from those conventionally used in the dyeing of keratin fibers. Among these coupling agents, mention may be made in particular of meta-phenylenediamines, meta-aminophenols, meta-diphenols, naphthalene-based coupling agents and heterocyclic coupling agents, and also the corresponding addition salts.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N—(β-hydroxyethyl)amino-3,4-methylenedioxybenzene, 2,6-bis(3-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, 2-methyl-5-aminophenol, 5-N—(β-hydroxyethyl)amino-2-methylphenol, 3-aminophenol and 3-amino-2-chloro-6-methylphenol, the corresponding addition salts with an acid and the corresponding mixtures.

In general, the addition salts of oxidation bases and coupling agents that may be used in the context of the invention are chosen in particular from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the dye composition, and preferably from 0.005% to 5% by weight relative to the total weight of the dye composition.

The coupling agent(s), if they are present, each advantageously represent from 0.001% to 10% by weight relative to the total weight of the dye composition, and preferably from 0.005% to 5% by weight relative to the total weight of the dye composition.

Direct Dyes

The dye composition may optionally comprise one or more direct dyes.

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of formulae (IIIa) and (III'a), the azo cationic dyes (IVa) and (IV'a) and the diazo cationic dyes (Va) below:

| | | |
|---|---|---|
| Het⁺—C(Rᵃ)=N—N(Rᵇ)—Ar, An⁻ (IIIa) | Het⁺—N(Rᵃ)—N=C(Rᵇ)—Ar, An⁻ (III'a) | Het⁺—N=N—Ar, An⁻ (IVa) |
| Ar⁺—N=N—Ar", An⁻ (IV'a) | and | Het⁺—N=N—Ar'—N=N—Ar, An⁻ (Va) | in which formulae (IIIa), (III'a), (IVa), (IV'a) and (Va):

Het⁺ represents a cationic heteroaryl radical, preferably bearing an endocyclic cationic charge, such as imidazolium, indolium or pyridinium, which is optionally substituted, preferably with one or more $(C_1$-$C_8)$alkyl groups such as methyl;

Ar⁺ represents an aryl radical, such as phenyl or naphthyl, bearing an exocyclic cationic charge, preferably ammonium, particularly tri$(C_1$-$C_8)$alkylammonium such as trimethylammonium;

Ar represents an aryl group, in particular phenyl, which is optionally substituted, preferably with one or more electron-donating groups such as i) optionally substituted $(C_1$-$C_8)$alkyl, ii) optionally substituted $(C_1$-$C_8)$alkoxy, iii) (di)$(C_1$-$C_8)$(alkyl)amino optionally substituted on the alkyl group(s) with a hydroxyl group, iv) aryl$(C_1$-$C_8)$alkylamino, v) optionally substituted N—$(C_1$-$C_8)$alkyl-N-aryl$(C_1$-$C_8)$alkylamino or, as a variant, Ar represents a julolidine group;

Ar' represents an optionally substituted divalent (hetero)arylene group such as phenylene, particularly para-phenylene, or naphthalene, which are optionally substituted, preferably with one or more $(C_1$-$C_8)$alkyl, hydroxyl or $(C_1$-$C_8)$alkoxy groups;

Ar" represents an optionally substituted (hetero)aryl group such as phenyl or pyrazolyl, which are optionally substituted, preferably with one or more $(C_1$-$C_8)$alkyl, hydroxyl, (di)$(C_1$-$C_8)$(alkyl)amino, $(C_1$-$C_8)$alkoxy or phenyl groups;

$R^a$ and $R^b$, which may be identical or different, represent a hydrogen atom or a $(C_1$-$C_8)$alkyl group, which is optionally substituted, preferably with a hydroxyl group; or, as a variant, the substituent $R^a$ with a substituent of Het⁺ and/or $R^b$ with a substituent of Ar and/or $R^a$ with $R^b$ form, together with the atoms that bear them, a (hetero)cycloalkyl; in particular, $R^a$ and $R^b$ represent a hydrogen atom or a $(C_1$-$C_4)$alkyl group, which is optionally substituted with a hydroxyl group;

An⁻ represents an anionic counterion, such as mesylate or halide.

Mention may be made in particular of the azo and hydrazono cationic dyes bearing an endocyclic cationic charge of formulae (IIIa), (III'a) and (IVa) as defined previously. More particularly those of formulae (IIIa), (III'a) and (IVa) derived from the dyes described in patent applications WO 95/15144, WO 95/01772 and EP-714954.

Preferably, the cationic part is derived from the following derivatives:

(IIIa-1)

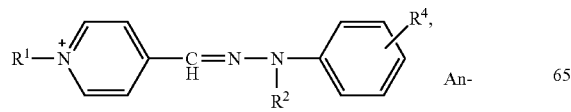

(IVa-1)

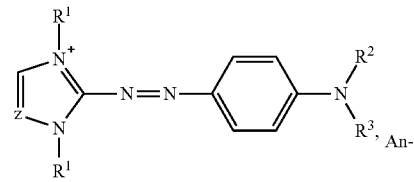

formulae (IIIa-1) and (IVa-1) with:

$R^1$ representing a $(C_1$-$C_4)$alkyl group such as methyl;

$R^2$ and $R^3$, which may be identical or different, represent a hydrogen atom or a $(C_1$-$C_4)$alkyl group, such as methyl; and $R^4$ represents a hydrogen atom or an electron-donating group such as an optionally substituted $(C_1$-$C_8)$alkyl, optionally substituted $(C_1$-$C_8)$alkoxy, or (di)$(C_1$-$C_8)$(alkyl)amino group optionally substituted on the alkyl group(s) with a hydroxyl group; in particular, $R^4$ represents a hydrogen atom;

Z represents a CH group or a nitrogen atom, preferably CH;

An⁻ represents an anionic counterion, such as mesylate or halide.

In particular, the dye of formulae (IIIa-1) and (IVa-1) is chosen from Basic Red 51, Basic Yellow 87 and Basic Orange 31 or corresponding derivatives:

Basic Red 51

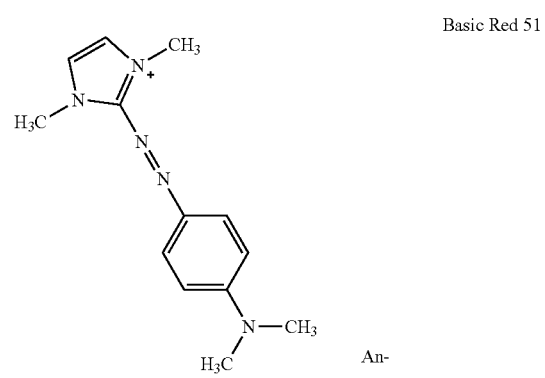

Basic Orange 31

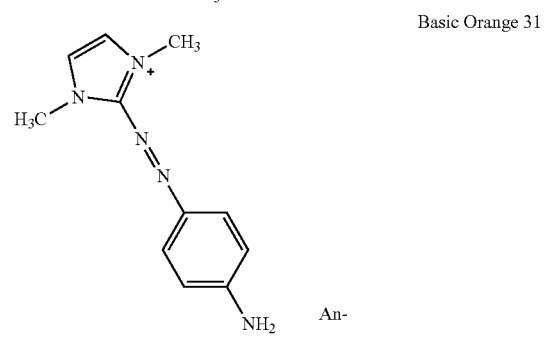

Basic Yellow 87

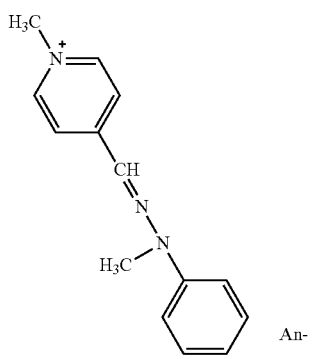

Among the natural direct dyes that may be used according to the invention, mention may be made of hennotannic acid, juglone, alizarin, purpurin, carminic acid, kermesic acid, purpurogallin, protocatechaldehyde, indigo, isatin, curcumin, spinulosin, apigenidin and orcein. Extracts or decoctions containing these natural dyes and in particular henna-based poultices or extracts may also be used.

When they are present, the direct dye(s) more particularly represent from 0.001% to 10% by weight and preferably from 0.005% to 5% by weight relative to the total weight of the dye composition.

The dyeing or bleaching composition may also optionally comprise one or more additives, different from the compounds described previously, among which mention may be made of cationic, anionic, nonionic or amphoteric polymers or mixtures thereof, antidandruff agents, antiseborrhea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, notably polymeric thickeners, opacifiers or nacreous agents, antioxidants, hydroxy acids, fragrances, preserving agents, pigments and ceramides.

Additional Features Regarding the Process

Composition (A) may be applied to wet or dry keratin fibers.

Bath Ratio

Composition (A) or the dyeing or bleaching composition may advantageously be applied to the keratin fibers in an amount ranging from 0.1 g to 10 g of composition (A) or of dyeing or bleaching composition per gram of keratin fibers.

Preferably, composition (A) may be applied to the keratin fibers in an amount ranging from 0.2 g to 5 g of composition (A) per gram of keratin fibers.

Leave-on Time Step

The process preferably also comprises, between steps i) and ii), a step i') consisting in leaving composition (A) to stand on the keratin fibers for a time ranging from 1 min to 60 min, more preferentially ranging from 3 min to 40 min and even more preferentially ranging from 3 min to 20 min.

The leave-on time step may take place at a temperature ranging from 15° C. to 45° C., preferably at room temperature (25° C.). The leave-on time may take place under an occlusive system. A nonlimiting example of an occlusive system that may be mentioned is an occlusive system of envelope type made of aluminum or plastic film or a hair cap with or without holes.

Rinsing and/or Drying Step

The process may also comprise, after step i) or i') and before step ii), a step of rinsing and/or drying the keratin fibers, preferably a drying step.

The term "rinsing step" means a step of rinsing with water.

The drying step may be performed using absorbent paper, a hairdryer or a styling hood or by drying naturally.

According to a preferred embodiment, the process does not comprise a rinsing step between step i) or i') and step ii).

According to a particularly preferred embodiment, the process does not comprise a rinsing step between step i) or i') and step ii), and comprises a drying step between step i) or i') and step ii), preferably a step of drying naturally.

Composition (A)

According to a second aspect, a subject of the present invention is composition (A) as defined previously.

Uses

According to a third aspect, a subject of the present invention is the use of a composition (A) as defined previously, as a pretreatment composition of a dyeing or bleaching process.

According to a fourth aspect, a subject of the present invention is the use of a composition (A) as defined previously, for protecting keratin fibers, preferably for protecting them against breakage, during a dyeing or bleaching treatment.

Multi-Compartment Device (Kit)

According to a fifth aspect, a subject of the present invention is a multi-compartment device (kit) comprising:
  a first compartment containing a composition (A) as defined previously; and
  a second compartment containing a composition comprising at least one chemical oxidizing agent; and
  optionally a third compartment containing a composition comprising at least one coloring agent chosen from oxidation dyes, direct dyes and mixtures thereof.

The optional technical features described previously concerning the chemical oxidizing agent and the coloring agent also apply to the compositions included in the second and third compartment.

EXAMPLES

The examples that follow allow the invention to be understood more clearly, without, however, being limiting in nature. In the examples that follow, unless otherwise indicated, all the amounts are shown as mass percentages relative to the total weight of the composition.

In the text that follows, the term "alkaline solubility (AS)" means the loss of mass of a sample of 100 mg of keratin fibers under the action of a decinormal sodium hydroxide solution for 30 minutes at 65° C.

Example 1

The following compositions were prepared:
Pretreatment Composition

TABLE 1

| Ingredients | A1 |
|---|---|
| Glycine | 10 |
| Sodium hydroxide (33% solution) | qs pH = 9 |
| Water | qs 100 |

Bleaching Powder

TABLE 2

| Ingredients | B |
|---|---|
| Potassium persulfate | 32.90 |
| Ammonium persulfate | 9.80 |
| Sodium silicate | 33.70 |
| Magnesium carbonate hydroxide | 9.20 |
| Disodium EDTA | 1.0 |
| Acrylates/C10-30 alkyl acrylate crosspolymer | 0.70 |
| Hydroxyethylcellulose | 0.70 |
| Glycine | 1.0 |
| Talc | 6.85 |
| Pigment | 0.25 |
| Dimethicone | 1.40 |
| Mineral oil | 2.50 |

Oxidizing Composition

TABLE 3

| Ingredients | C |
|---|---|
| Tetrasodium pyrophosphate | 0.05 |
| Sodium salicylate | 0.05 |
| Tetrasodium etidronate | 0.12 |
| Mineral oil | 17.0 |
| Cetearyl alcohol | 3.15 |
| PEG-40 hydrogenated castor oil | 0.90 |
| Sodium cetearyl sulfate | 0.45 |
| Hydrogen peroxide | 9.0 |
| Phosphoric acid | qs pH = 2.4 ± 0.2 |
| Water | qs 100 |

Application Protocol

Two identical locks of moderately sensitized hair (AS 20) were used: lock 1 (Control) and lock 2 (Invention). Lock 1 is a control lock which undergoes only a bleaching treatment, whereas lock 2 is a lock which undergoes a pretreatment before the bleaching treatment, using the pretreatment composition A1.

Each of the locks was combed with a comb according to the following routine: 10 strokes at the coarse-toothed end and then 10 strokes at the fine-toothed end so as to remove the unattached hair strands.

Each of the locks was weighed and their mass ($m_0$) was noted.

The locks were then placed on a hotplate thermostatically regulated at 33° C.

The pretreatment composition A1 was applied to lock 2 with a bath ratio of 2 g of composition per 1 g of hair.

After a leave-on time of 5 minutes, lock 2 was blotted dry using a Kimtech 7505 absorbent paper towel.

A bleaching composition was prepared by mixing 1 part by weight of composition B with 1.5 parts by weight of composition C and was then applied to lock 1 and to lock 2. The bath ratio is 10 g of composition per 1 g of hair.

Each of the locks was then wrapped in aluminum foil and then returned onto the hotplate at 33° C.

After a leave-on time of 50 minutes, the locks were rinsed and washed with L'Oréal Blond Studio shampoo.

The locks were dried in an oven regulated at 60° C. for 30 minutes.

On exiting the oven, the locks were combed: 10 strokes with the coarse-toothed end and 10 strokes with the fine-toothed end.

All these steps were repeated twice, including the application of the pretreatment composition A1 to lock 2, which corresponds to a total of three applications on each lock.

Finally, each of the locks was weighed and their mass ($m_1$) was noted.

Evaluation of the Breakage of the Hair

The percentage of breakage of each of the locks is expressed by means of the following equation:

$$\% \text{ breakage} = 100 - \frac{m_1}{m_0} * 100$$

with:

$m_0$: initial mass of the lock before any treatment $m_1$: mass recorded after total treatment.

Results

The percentage of breakage of each of the locks is indicated in the following table:

TABLE 4

| Type of lock | $m_0$ (g) | $m_1$ (g) | % breakage |
|---|---|---|---|
| Lock 1 (Control) | 2.9184 | 1.1604 | 60.23 |
| Lock 2 (Invention) | 2.9084 | 2.4217 | 16.73 |

The results show a marked decrease in breakage of the hair for the lock treated by means of the process according to the present invention comprising a pretreatment step using a composition comprising glycine at high concentration, relative to the same process without the pretreatment step.

Example 2

This example demonstrates the advantage in terms of the reduction of hair breakage provided by the process according to the present invention in which locks of sensitized hair enriched with copper are treated.

Specifically, certain heavy metals present in tap water, such as copper, can accumulate over time on the hair during successive washes and lead to degradation of the constituent proteins of the hair. This degradation takes place in particular during dyeing or bleaching treatments using a chemical oxidizing agent such as hydrogen peroxide. The presence of copper on the hair may lead to the formation of hydroxyl radicals which may be responsible for the denaturing of the constituent proteins of the hair.

The following pretreatment compositions were prepared:

TABLE 5

| Ingredients | A2 (Invention) | A3 (Invention) | A4 (Invention) |
|---|---|---|---|
| Glycine | $6.66 \times 10^{-2}$ mol % | — | — |
| L-Serine | — | $6.66 \times 10^{-2}$ mol % | — |
| L-Proline | — | — | $6.66 \times 10^{-2}$ mol % |
| Sodium hydroxide (33% solution) | qs pH = 9 | qs pH = 9 | qs pH = 9 |
| Water | qs 100 | qs 100 | qs 100 |

TABLE 6

| Ingredients | A5 (Invention) | A6 (Invention) | A7 (Invention) |
|---|---|---|---|
| L-Methionine | $6.66 \times 10^{-2}$ mol % | — | — |
| L-Arginine | — | $6.66 \times 10^{-2}$ mol % | — |
| L-Lysine | — | — | $6.66 \times 10^{-2}$ mol % |
| Sodium hydroxide (33% solution) | qs pH = 9 | qs pH = 9 | qs pH = 9 |
| Water | qs 100 | qs 100 | qs 100 |

TABLE 7

| Ingredients | A8 (Comparative) | A9 (Comparative) | A10 (Comparative) |
|---|---|---|---|
| L-Alanine | $6.66 \times 10^{-2}$ mol % | — | — |
| L-Cysteine | — | $6.66 \times 10^{-2}$ mol % | — |
| L-Histidine | — | — | $6.66 \times 10^{-2}$ mol % |
| Sodium hydroxide (33% solution) | qs pH = 9 | qs pH = 9 | qs pH = 9 |
| Water | qs 100 | qs 100 | qs 100 |

TABLE 8

| Ingredients | A11 (Comparative) | A12 (Comparative) | A13 (Comparative) |
|---|---|---|---|
| L-Aspartic acid | $6.66 \times 10^{-2}$ mol % | — | — |
| L-Glutamic acid | — | $6.66 \times 10^{-2}$ mol % | — |
| L-Tyrosine | — | — | $6.66 \times 10^{-2}$ mol % |
| Sodium hydroxide (33% solution) | qs pH = 9 | qs pH = 9 | qs pH = 9 |
| Water | qs 100 | qs 100 | qs 100 |

Preparation of the Locks

Thirteen identical locks of moderately sensitized hair (AS 20) were enriched with 10 000 ppm of copper using a copper(II) sulfate pentahydrate $CuSO_4 \cdot 5H_2O$ solution (minimum purity of 99%) from Prolabo®.

Application Protocol

Among the thirteen locks, lock 3 is a control lock which undergoes only a bleaching treatment, whereas locks 4 to 15 are locks which undergo a pretreatment before the bleaching treatment, using the pretreatment compositions A2 to A13.

Each of the locks was combed with a comb according to the following routine: 10 strokes at the coarse-toothed end and then 10 strokes at the fine-toothed end so as to remove the unattached hair strands.

Each of the locks was weighed and their mass ($m_0$) was noted.

The locks were then placed on a hotplate thermostatically regulated at 33° C.

The pretreatment compositions A2 to A13 were applied to locks 4 to 15 with a bath ratio of 2 g of composition per 1 g of hair.

After a leave-on time of 5 minutes, locks 4 to 15 were blotted dry using a Kimtech 7505 absorbent paper towel.

A bleaching composition was prepared by mixing 1 part by weight of composition B of Example 1 with 1.5 parts by weight of composition C of Example 1 and was then applied to locks 3 to 15. The bath ratio is 10 g of composition per 1 g of hair.

After a leave-on time of 50 minutes at 33° C., the locks were rinsed and washed with L'Oréal Blond Studio shampoo.

The locks were dried in an oven regulated at 60° C. for 30 minutes.

On exiting the oven, the locks were combed: 10 strokes with the coarse-toothed end and 10 strokes with the fine-toothed end.

Finally, each of the locks was weighed and their mass ($m_1$) was noted.

Evaluation of the Breakage of the Hair

The percentage of breakage of each of the locks is expressed by means of the following equation:

$$\% \text{ breakage} = 100 - \frac{m_1}{m_0} * 100$$

with:
$m_0$: initial mass of the lock before any treatment
$m_1$: mass recorded after total treatment.

Results

The percentage of breakage of each of the locks is indicated in the following table:

| Type of lock | Amino acid | MM (mol/g) | C (g %) | $m_0$ (g) | $m_1$ (g) | % breakage |
|---|---|---|---|---|---|---|
| Lock 3 (Control) | / | / | / | 1.3302 | 1.1093 | 16.61 |
| Lock 4 (Invention) | 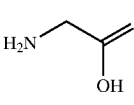 Glycine | 75 | 5 | 1.3582 | 1.2848 | 5.40 |
| Lock 5 (Invention) | 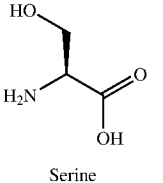 Serine | 105 | 6.9 | 1.3927 | 1.3105 | 5.90 |

-continued
| Type of lock | Amino acid | MM (mol/g) | C (g %) | $m_0$ (g) | $m_1$ (g) | % breakage |
|---|---|---|---|---|---|---|
| Lock 6 (Invention) | 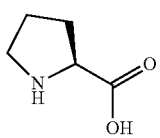 Proline | 115 | 7.6 | 1.3684 | 1.2981 | 5.14 |
| Lock 7 (Invention) | 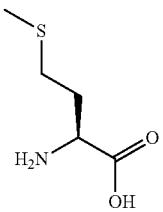 Methionine | 149 | 9.8 | 1.4312 | 1.3487 | 5.76 |
| Lock 8 (Invention) | 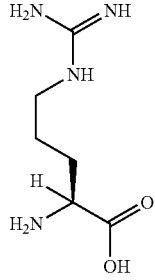 Arginine | 174 | 11.5 | 1.2717 | 1.173 | 7.76 |
| Lock 9 (Invention) | 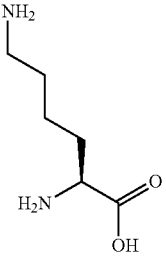 Lysine | 146 | 9.6 | 1.3273 | 1.267 | 4.54 |
| Lock 10 (Comparative) | 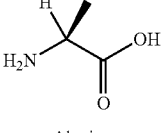 Alanine | 89 | 5.9 | 1.3622 | 1.208 | 11.32 |
| Lock 11 (Comparative) | 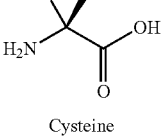 Cysteine | 121 | 8 | 1.3468 | 1.1909 | 11.58 |

-continued

| Type of lock | Amino acid | MM (mol/g) | C (g %) | $m_0$ (g) | $m_1$ (g) | % breakage |
|---|---|---|---|---|---|---|
| Lock 12 (Comparative) | Histidine | 155 | 10.23 | 1.2471 | 0.994 | 20.30 |
| Lock 13 (Comparative) | Aspartic acid | 133 | 8.8 | 1.2959 | 1.066 | 17.74 |
| Lock 14 (Comparative) | Glutamic acid | 147 | 9.7 | 1.4137 | 1.1869 | 16.04 |
| Lock 15 (Comparative) | Tyrosine | 181 | 11.9 | 1.3154 | 1.1025 | 16.19 |

The results show that the amino acids chosen from the compounds of formula ($I_1$) used as a pretreatment according to the present invention efficiently protect against the breakage of hair comprising high contents of copper. It is noted that the hair breakage is reduced by at least 50% relative to the lock treated by bleaching without pretreatment.

Example 3

The following compositions were prepared:
Alkaline Composition (D)

TABLE 9

| Ingredients | D |
|---|---|
| Mineral oil | 60 |
| Oxyethylenated (5 OE) decyl alcohol | 1.20 |
| Cetyl palmitate | 2 |
| Mixture of linear C18-24 fatty alcohols (Nafol 2022 EN sold by the company Sasol) | 2 |

TABLE 9-continued

| Ingredients | D |
|---|---|
| Oxyethylenated (60 OE) (C16/C18) cetylstearyl alcohol myristyl glycol ether | 0.01 |
| Oxyethylenated (20 OE) oleyl alcohol | 4 |
| Oxyethylenated (10 OE) oleyl alcohol | 1 |
| Carboxyvinyl polymer synthesized in an ethyl acetate/cyclohexane mixture (Carbopol ® 980 Polymer sold by the company Lubrizol) | 0.10 |
| Glycerol | 5 |
| Non-stabilized polydimethyldiallylammonium chloride at 40% in water (Merquat ™ 100 Polymer sold by the company Lubrizol) | 0.96 |
| Poly[(dimethyliminio)-1,3-propanediyl(dimethyliminio)-1,6-hexanediyl dichloride] as an aqueous 60% solution (Mexomer PO sold by the company Noveal) | 0.48 |
| Vitamin C: Ascorbic acid | 0.12 |
| Ethylenediaminetetraacetic acid | 0.20 |
| Powdered sodium metabisulfite | 0.22 |

TABLE 9-continued

| Ingredients | D |
|---|---|
| Pure monoethanolamine | 6.27 |
| Deionized water | qs 100 |

Oxidizing Composition (E)

TABLE 10

| Ingredient | E |
|---|---|
| Cetylstearyl alcohol (30/70 C16/C18) | 6 |
| Oxyethylenated (20 OE) stearyl alcohol | 5 |
| Mineral oil | 50 |
| Oxyethylenated (4 OE) rapeseed acid amide | 1.30 |
| Vitamin E: DL-α-Tocopherol | 0.10 |
| Glycerol | 0.50 |
| Tetrasodium pyrophosphate decahydrate | 0.04 |
| Hydrogen peroxide as a 50% solution (200 vol. aqueous hydrogen peroxide solution) | 24 |
| Etidronic acid, tetrasodium salt, as an aqueous 30% solution | 0.20 |
| Sodium salicylate | 0.035 |
| Deionized water | qs 100 |
| Phosphoric acid | qs pH = 2.2 |

Preparation of the Locks

Five identical locks of moderately sensitized hair (AS 20) were enriched with 10 000 ppm of copper using a copper(II) sulfate pentahydrate $CuSO_4 \cdot 5H_2O$ solution (minimum purity of 99%) from Prolabo®.

Application Protocol

Among the five locks, lock 16 is a control lock which undergoes only a bleaching treatment, whereas locks 17 to 20 are locks which undergo a pretreatment before the bleaching treatment, using the pretreatment compositions A2 to A5 of Example 2.

Each of the locks was combed with a comb according to the following routine: 10 strokes at the coarse-toothed end and then 10 strokes at the fine-toothed end so as to remove the unattached hair strands.

Each of the locks was weighed and their mass ($m_0$) was noted.

The locks were then placed on a hotplate thermostatically regulated at 33° C.

The pretreatment compositions A2 to A5 were applied to locks 17 to 20 with a bath ratio of 2 g of solution per 1 g of hair.

After a leave-on time of 5 minutes, the locks were blotted dry using a Kimtech 7505 absorbent paper towel.

A bleaching composition was prepared by mixing 1 part by weight of composition D with 2 parts by weight of composition E (pH of the mixture equal to 10±0.2) and was then applied to locks 16 to 20. The bath ratio is 10 g of composition per 1 g of hair.

After a leave-on time of 50 minutes at 33° C., the locks were rinsed and washed with Inoa Post shampoo.

The locks were dried in an oven regulated at 60° C. for 30 minutes.

On exiting the oven, the locks were combed: 10 strokes with the coarse-toothed end and 10 strokes with the fine-toothed end.

Finally, each of the locks was weighed and their mass ($m_1$) was noted.

Evaluation of the Breakage of the Hair

The percentage of breakage of each of the locks is expressed by means of the following equation:

$$\% \text{ breaking} = 100 - \frac{m_1}{m_0} * 100$$

with:
$m_0$: initial mass of the lock before any treatment
$m_1$: mass recorded after total treatment.

Results

The percentage of breakage of each of the locks is indicated in the following table:

| Type of lock | Amino acid | MM (mol/g) | C (g %) | $m_0$ (g) | $m_1$ (g) | % breakage |
|---|---|---|---|---|---|---|
| Lock 16 (Control) | / | / | / | 1.4928 | 0.9004 | 39.68 |
| Lock 17 (Invention) | Glycine | 75 | 5 | 1.3162 | 1.2562 | 4.56 |
| Lock 18 (Invention) | Serine | 105 | 6.9 | 1.3678 | 1.3192 | 3.55 |

-continued

| Type of lock | Amino acid | MM (mol/g) | C (g %) | $m_0$ (g) | $m_1$ (g) | % breakage |
|---|---|---|---|---|---|---|
| Lock 19 (Invention) | 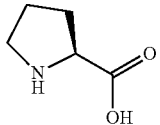  Proline | 115 | 7.6 | 1.3661 | 1 0000 | 5.36 |
| Lock 20 (Invention) | 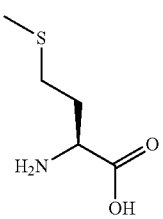  Methionine | 149 | 9.8 | 1.3459 | 1 0799 | 5.39 |

The results show that the amino acids chosen from the compounds of formula ($I_1$) used as a pretreatment according to the present invention efficiently protect against the breakage of hair comprising high contents of copper.

Example 4

The following compositions were prepared:
Lightening Compositions

TABLE 11

| Ingredients | C1 (Invention) | C2 (Comparative) |
|---|---|---|
| Mineral oil | 53.8 | 53.8 |
| Ceteth-2 | 1 | 1 |
| Decyl Glucoside as an aqueous 53% solution (Plantacare 2000 UP sold by the company BASF) | 2 | 2 |
| PEG-150/Decyl Alcohol/SMDI Copolymer in a propylene glycol/water mixture (Aculyn 44 Polymer sold by the company Dow Chemical) | 1 | 1 |
| Polyquaternium-67 | 0.20 | 0.20 |
| Pure monoethanolamine | 4.35 | 4.35 |
| Glycine | — | 3.2 |
| Sodium Hydroxide (33% solution) | — | qs pH = 11.7 |
| Water | qs 100 | qs 100 |
| pH | 11.7 | 11.7 |

TABLE 12

| Ingredients | A14 |
|---|---|
| Glycine | 8 |
| Sodium Hydroxide (33% solution) | qs pH = 9 |
| Water | qs 100 |

Application Protocol of the Pretreatment Composition 5.4 g of the pretreatment composition A14 were applied to a 2.7 g lock of tone depth 4 Caucasian hair (Lock 1).

Therefore, the amount of glycine in contact with lock 1 is 0.16 g/g of hair.

After a leave-on time of 5 minutes, lock 1 was blotted dry using a Kimtech 7505 absorbent paper towel.
Application Protocol of the Lightening Compositions One part of composition C1 was mixed with one part of L'Oréal Professionnel Inoa 30-Volume Developer. 27 g of the resulting mixture was then applied to lock 1.

One part of composition C2 was mixed with one part of L'Oréal Professionnel Inoa 30-Volume Developer. 27 g of the resulting mixture was then applied to a 2.7 g lock of tone depth 4 Caucasian hair (Lock 2). Therefore, the amount of glycine in contact with lock 2 is also 0.16 g/g of hair.

The two locks were then placed on a hotplate thermostatically regulated at 33° C.

After a leave-on time of 50 min, the locks were rinsed and washed with L'Oréal Professionnel Inoa Post shampoo.

The locks were dried in an oven regulated at 60° C. for 30 minutes.

Colorimetric Measurements

The measurements were taken using a Minolta CM2600d spectrophotometer (illuminant D65, angle 10°, specular component included) in the CIELab system.

In this system, L* represents the lightness: the higher the value of L*, the more the lock is lightened.

Results

TABLE 13

| Type of lock | L* |
|---|---|
| Untreated tone depth 4 Caucasian hair lock | 20.67 |
| Lock 1 (Invention) | 29.52 |
| Lock 2 (Comparative) | 25.99 |

The process according to the invention where glycine is applied as a pretreatment composition results in a higher value of L*, and thus greater lightening than the comparative process where glycine is directly included in the lightening composition. Hence, the process according to the invention avoids impairment of the lightening of the hair.

Example 5

The following compositions were prepared:
Lightening Compositions

TABLE 14

| Ingredients | C3 (Invention) | C4 (Comparative) |
|---|---|---|
| Ammonium Hydroxide (40% solution) | 20 | 20 |
| Glycine | — | 16 |
| Citric Acid | qs pH = 10.5 | — |
| Sodium Hydroxide (33% solution) | — | qs pH = 10.5 |
| Water | qs 100 | qs 100 |

Application Protocol of the Pretreatment Composition 6.4 g of the pretreatment composition A14 of example 4 were applied to a 2.7 g lock of tone depth 4 Caucasian hair (Lock 3).

Therefore, the amount of glycine in contact with lock 3 is 0.2 g/g of hair.

After a leave-on time of 5 minutes, lock 3 was blotted dry using a Kimtech 7505 absorbent paper towel.

Application Protocol of the Lightening Compositions

One part of composition C3 was mixed with two parts of L'Oréal Professionnel 40-Volume Oxydant Crème Developer. 10 g of the resulting mixture was then applied to lock 3.

One part of composition C4 was mixed with two parts of L'Oréal Professionnel 40-Volume Oxydant Crème Developer. 10 g of the resulting mixture was then applied to a 2.7 g lock of tone depth 4 Caucasian hair (Lock 4). Therefore, the amount of glycine in contact with lock 4 is also 0.2 g/g of hair.

The two locks were then placed on a hotplate thermostatically regulated at 33° C.

After a leave-on time of 50 min, the locks were rinsed and washed with Garnier Ultra-doux shampoo.

The locks were dried in an oven regulated at 60° C. for 30 minutes.

Colorimetric Measurements

The measurements were taken using a Minolta CM2600d spectrophotometer (illuminant D65, angle 10°, specular component included) in the CIELab system.

In this system, L* represents the lightness: the higher the value of L*, the more the lock is lightened.

Results

TABLE 15

| Type of lock | L* |
|---|---|
| Untreated tone depth 4 Caucasian hair lock | 19.2 |
| Lock 3 (Invention) | 26.65 |
| Lock 4 (Comparative) | 24.35 |

The process according to the invention where glycine is applied as a pretreatment composition results in a higher value of L*, and thus greater lightening than the comparative process where glycine is directly included in the lightening composition. Hence, the process according to the invention avoids impairment of the lightening of the hair.

The invention claimed is:

1. A method for bleaching and/or dyeing keratin fibers, comprising:
   (i) applying to the keratin fibers a composition (A) comprising at least one amino acid chosen from compounds of formula ($I_1$), salts thereof, and mixtures of two or more thereof:

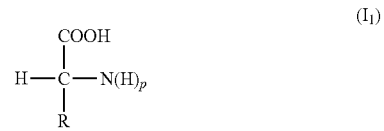

$$(I_1)$$

wherein in formula ($I_1$):
   p represents an integer equal to 1 or 2;
   when p=1, R forms a saturated 5- to 8-membered ring with the nitrogen atom; and
   when p=2, R represents:
      a hydrogen atom; or
      a ($C_1$-$C_{12}$)alkyl group, interrupted with at least one heteroatom or group chosen from —S—, —NH—, and —C(NH)—, and/or substituted with at least one group chosen from hydroxyl, amino, and —NH—C(NH)—$NH_2$; and
   wherein the total amount of amino acids present in composition (A) is at least 5% by weight, relative to the total weight of composition (A); and
   (ii) applying to the keratin fibers a bleaching and/or dyeing composition.

2. The method according to claim 1, wherein composition (A) comprises at least one amino acid chosen from glycine, proline, methionine, serine, arginine, lysine, salts thereof, and mixtures of two or more thereof.

3. The method according to claim 1, wherein the total amount of amino acids of formula ($I_1$) present in composition (A) ranges from 5% to 20% by weight, relative to the total weight of composition (A).

4. The method according to claim 1, wherein the pH of composition (A) ranges from 2 to 11.

5. The method according to claim 1, wherein composition (A) further comprises at least one cationic polymer and/or at least one amino silicone.

6. The method according to claim 1, wherein composition (A) further comprises at least one surfactant, wherein the total amount of surfactants is less than 5% by weight, relative to the total weight of composition (A).

7. The method according to claim 1, wherein composition (A) further comprises at least one organic solvent.

8. The method according to claim 1, wherein composition (A) further comprises at least one alkaline agent.

9. The method according to claim 1, wherein the dyeing composition, the bleaching composition, or both comprise at least one chemical oxidizing agent.

10. The method according to claim 1, wherein the composition applied during step (ii) is a dye composition comprising at least one coloring agent chosen from oxidation dyes, direct dyes, and mixtures of two or more thereof.

11. The method according to claim 1, further comprising, between steps (i) and (ii), a step (i') of leaving composition (A) on the keratin fibers for a leave-on time ranging from 1 minute to 60 minutes.

12. The method according to claim 11, further comprising, after step (i) and/or step (i') and before step (ii), rinsing and/or drying the keratin fibers.

13. The method according to claim 1, wherein the method does not comprise a rinsing step between step (i) and step (ii).

14. The method according to claim 1, comprising:
(i) applying to hair a composition (A) comprising at least one amino acid chosen from compounds of formula ($I_1$), salts thereof, and mixtures of two or more thereof:

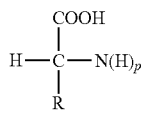

(I_1)

wherein in formula ($I_1$):
p represents an integer equal to 1 or 2;
when p=1, R forms a saturated 5- to 8-membered ring with the nitrogen atom; and
when p=2, R represents:
a hydrogen atom; or
a ($C_1$-$C_{12}$)alkyl group, interrupted with at least one heteroatom or group chosen from —S—, —NH—, and —C(NH)—, and/or substituted with at least one group chosen from hydroxyl, amino, and —NH—C(NH)—$NH_2$;
wherein the total amount of amino acids of formula ($I_1$) present in composition (A) ranges from 5% to 15% by weight, relative to the total weight of composition (A); and
wherein composition (A) has a pH ranging from 8 to 10;
(i') leaving composition (A) on the hair for a leave-on time ranging from 1 minute to 60 minutes;
(i") optionally rinsing and/or drying the hair; and
(ii) subsequently applying to the hair a composition (B) comprising at least one chemical oxidizing agent.

15. The method according to claim 14, wherein composition (A) further comprises at least one alkaline agent and at least one organic solvent.

16. The method according to claim 14, wherein composition (B) further comprises at least one hair dye chosen from oxidation dyes, direct dyes, and mixtures of two or more thereof.

17. A composition (A) comprising at least one amino acid chosen from compounds of formula ($I_1$), salts thereof, and mixtures of two or more thereof:

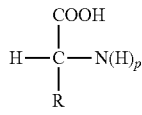

(I_1)

wherein in formula ($I_1$):
p represents an integer equal to 1 or 2;
when p=1, R forms a saturated 5- to 8-membered ring with the nitrogen atom; and
when p=2, R represents:
a hydrogen atom; or
a ($C_1$-$C_{12}$)alkyl group, interrupted with at least one heteroatom or group chosen from —S—, —NH— and —C(NH)—, and/or substituted with at least one group chosen from hydroxyl, amino, and —NH—C(NH)—$NH_2$; and
wherein the total amount of amino acids present in composition (A) is at least 5% by weight, relative to the total weight of composition (A).

18. The composition according to claim 17, wherein the total amount of amino acids of formula ($I_1$) ranges from 5% to 20% by weight, relative to the total weight of composition (A).

19. The composition according to claim 17, wherein the pH of the composition ranges from 4 to 10.

20. A device or kit comprising:
a) a first compartment or container comprising a composition (A), wherein composition (A) comprises at least one amino acid chosen from compounds of formula ($I_1$), salts thereof, and mixtures of two or more thereof:

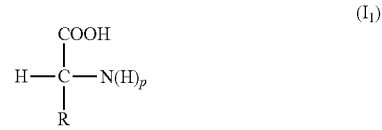

(I_1)

wherein in formula ($I_1$):
p represents an integer equal to 1 or 2;
when p=1, R forms a saturated 5- to 8-membered ring with the nitrogen atom; and
when p=2, R represents:
a hydrogen atom; or
a ($C_1$-$C_{12}$)alkyl group, interrupted with at least one heteroatom or group chosen from —S—, —NH—, and —C(NH)—, and/or substituted with at least one group chosen from hydroxyl, amino, and —NH—C(NH)—$NH_2$; and
wherein the total amount of amino acids present in composition (A) is at least 5% by weight, relative to the total weight of composition (A);
b) a second compartment or container comprising a composition (B) comprising at least one chemical oxidizing agent; and
c) optionally a third compartment or container containing a composition (C) comprising at least one coloring agent chosen from oxidation dyes, direct dyes, and mixtures of two or more thereof.

* * * * *